(12) United States Patent
Gonzalez et al.

(10) Patent No.: US 8,444,690 B2
(45) Date of Patent: *May 21, 2013

(54) BRONCHOSCOPIC REPAIR OF AIR LEAKS IN A LUNG

(75) Inventors: Hugo Xavier Gonzalez, Woodinville, WA (US); Steven C Springmeyer, Bellevue, WA (US); William A. Sirokman, Kirkland, WA (US)

(73) Assignee: Spiration, Inc., Redmond, WA (US)

( * ) Notice: Subject to any disclaimer, the term of this patent is extended or adjusted under 35 U.S.C. 154(b) by 43 days.

This patent is subject to a terminal disclaimer.

(21) Appl. No.: 13/005,444

(22) Filed: Jan. 12, 2011

(65) Prior Publication Data

US 2011/0208228 A1 Aug. 25, 2011

Related U.S. Application Data

(60) Continuation of application No. 12/398,122, filed on Mar. 4, 2009, now Pat. No. 7,887,585, which is a division of application No. 10/745,401, filed on Dec. 22, 2003, now Pat. No. 7,533,671.

(60) Provisional application No. 60/493,933, filed on Aug. 8, 2003.

(51) Int. Cl.
*A61F 2/20* (2006.01)

(52) U.S. Cl.
USPC ............................................................ 623/9

(58) Field of Classification Search
USPC .............................. 623/9; 128/207.12–207.16
See application file for complete search history.

(56) References Cited

U.S. PATENT DOCUMENTS

| | | | |
|---|---|---|---|
| 2,981,254 A | 4/1961 | Vanderbilt |
| 3,540,431 A | 11/1970 | Modin-Udin |
| 3,657,744 A | 4/1972 | Ersek |
| 3,788,327 A | 1/1974 | Donowitz et al. |
| 3,874,388 A | 4/1975 | King et al. |
| 4,014,318 A | 3/1977 | Dockum et al. |

(Continued)

FOREIGN PATENT DOCUMENTS

| | | |
|---|---|---|
| EP | 1151729 A1 | 11/2001 |
| EP | 1157663 A1 | 11/2001 |

(Continued)

OTHER PUBLICATIONS

Dillard et al., "Evaluation of a Novel Intra-bronchial Valve Device to Produce Lung Volume Reduction," Poster shown at conference in Jun. 2002.

(Continued)

*Primary Examiner* — Suzette J Gherbi
(74) *Attorney, Agent, or Firm* — Knobbe, Martens, Olson & Bear LLP (57) ABSTRACT

Systems and devices for minimally invasively treating an air leak in a lung comprise the steps of detecting an air leak in a lung; locating an airway in fluid communication with the air leak, introducing a bronchoscope into a patient's airway to a position adjacent the target section and occluding an airway upstream of the air leak for a period of time. The airway occlusion device is preferably removed after the air leak has substantially permanently healed. The occluding device may be a one-way valve. The occluding device may also comprise strut members and anchors that penetrate an airway wall.

8 Claims, 5 Drawing Sheets

U.S. PATENT DOCUMENTS

| | | |
|---|---|---|
| 4,086,665 A | 5/1978 | Poirier |
| 4,212,463 A | 7/1980 | Repinski et al. |
| 4,250,873 A | 2/1981 | Bonnet |
| 4,302,854 A | 12/1981 | Runge |
| 4,710,192 A | 12/1987 | Liotta et al. |
| 4,732,152 A | 3/1988 | Wallsten et al. |
| 4,759,758 A | 7/1988 | Gabbay |
| 4,795,449 A | 1/1989 | Schneider et al. |
| 4,808,183 A | 2/1989 | Panje |
| 4,819,664 A | 4/1989 | Nazari |
| 4,830,003 A | 5/1989 | Wolff et al. |
| 4,832,680 A | 5/1989 | Haber et al. |
| 4,846,836 A | 7/1989 | Reich |
| 4,850,999 A | 7/1989 | Planck |
| 4,852,568 A | 8/1989 | Kensey |
| 4,877,025 A | 10/1989 | Hanson |
| 4,934,999 A | 6/1990 | Bader |
| 4,968,294 A | 11/1990 | Salama |
| 5,061,274 A | 10/1991 | Kensey |
| 5,116,360 A | 5/1992 | Pinchuk et al. |
| 5,116,564 A | 5/1992 | Jansen et al. |
| 5,123,919 A | 6/1992 | Sauter et al. |
| 5,151,105 A | 9/1992 | Kwan-Gett |
| 5,161,524 A | 11/1992 | Evans |
| 5,306,234 A | 4/1994 | Johnson |
| 5,352,240 A | 10/1994 | Ross |
| 5,358,518 A | 10/1994 | Camilli |
| 5,366,478 A | 11/1994 | Brinkerhoff et al. |
| 5,382,261 A | 1/1995 | Palmaz |
| 5,392,775 A | 2/1995 | Adkins et al. |
| 5,409,019 A | 4/1995 | Wilk |
| 5,411,507 A | 5/1995 | Heckele |
| 5,411,552 A | 5/1995 | Andersen et al. |
| 5,413,599 A | 5/1995 | Imachi et al. |
| 5,417,226 A | 5/1995 | Juma |
| 5,445,626 A | 8/1995 | Gigante |
| 5,486,154 A | 1/1996 | Kelleher |
| 5,499,995 A | 3/1996 | Teirstein |
| 5,500,014 A | 3/1996 | Quijano et al. |
| 5,549,626 A | 8/1996 | Miller et al. |
| 5,549,628 A | 8/1996 | Cooper et al. |
| 5,562,608 A | 10/1996 | Sekins et al. |
| 5,645,565 A | 7/1997 | Rudd et al. |
| 5,660,175 A | 8/1997 | Dayal |
| 5,662,713 A | 9/1997 | Andersen et al. |
| 5,683,451 A | 11/1997 | Lenker et al. |
| 5,693,089 A | 12/1997 | Inoue |
| 5,697,968 A | 12/1997 | Rogers et al. |
| 5,702,409 A | 12/1997 | Rayburn et al. |
| 5,725,519 A | 3/1998 | Penner et al. |
| 5,752,965 A | 5/1998 | Francis et al. |
| 5,755,770 A | 5/1998 | Ravenscroft |
| 5,797,960 A | 8/1998 | Stevens et al. |
| 5,800,339 A | 9/1998 | Salama |
| 5,840,081 A | 11/1998 | Andersen et al. |
| 5,851,232 A | 12/1998 | Lois |
| 5,855,587 A | 1/1999 | Hyon et al. |
| 5,855,597 A | 1/1999 | Jayaraman |
| 5,855,601 A | 1/1999 | Bessler et al. |
| 5,944,738 A | 8/1999 | Amplatz et al. |
| 5,947,997 A | 9/1999 | Pavcnik et al. |
| 5,954,766 A | 9/1999 | Zadno-Azizi et al. |
| 5,957,949 A | 9/1999 | Leonhardt et al. |
| 5,972,009 A | 10/1999 | Fortier et al. |
| 5,976,158 A | 11/1999 | Adams et al. |
| 5,976,174 A | 11/1999 | Ruiz |
| 5,984,965 A | 11/1999 | Knapp et al. |
| 6,003,517 A | 12/1999 | Sheffield et al. |
| 6,007,575 A | 12/1999 | Samuels |
| 6,009,614 A | 1/2000 | Morales |
| 6,020,380 A | 2/2000 | Killian |
| 6,027,525 A | 2/2000 | Suh et al. |
| 6,045,560 A | 4/2000 | McKean et al. |
| 6,051,022 A | 4/2000 | Cai et al. |
| 6,068,635 A | 5/2000 | Gianotti |
| 6,068,638 A | 5/2000 | Makower |
| 6,077,291 A | 6/2000 | Das |
| 6,083,255 A | 7/2000 | Laufer et al. |
| 6,096,027 A | 8/2000 | Layne |
| 6,099,551 A | 8/2000 | Gabbay |
| 6,123,663 A | 9/2000 | Rebuffat |
| 6,135,729 A | 10/2000 | Aber |
| 6,135,991 A | 10/2000 | Muni et al. |
| 6,141,855 A | 11/2000 | Morales |
| 6,162,245 A | 12/2000 | Jayaraman |
| 6,168,614 B1 | 1/2001 | Andersen et al. |
| 6,174,323 B1 | 1/2001 | Biggs |
| 6,183,520 B1 | 2/2001 | Pintauro et al. |
| 6,200,333 B1 | 3/2001 | Laufer |
| 6,206,918 B1 | 3/2001 | Campbell et al. |
| 6,234,996 B1 | 5/2001 | Bagaoisan et al. |
| 6,240,615 B1 | 6/2001 | Kimes et al. |
| 6,245,102 B1 | 6/2001 | Jayaraman |
| 6,258,100 B1 | 7/2001 | Alferness et al. |
| 6,270,527 B1 | 8/2001 | Campbell et al. |
| 6,287,290 B1 | 9/2001 | Perkins et al. |
| 6,287,334 B1 | 9/2001 | Moll et al. |
| 6,293,951 B1 | 9/2001 | Alferness et al. |
| 6,302,893 B1 | 10/2001 | Limon et al. |
| 6,312,407 B1 | 11/2001 | Zadno-Azizi et al. |
| 6,325,777 B1 | 12/2001 | Zadno-Azizi et al. |
| 6,325,778 B1 | 12/2001 | Zadno-Azizi et al. |
| 6,327,772 B1 | 12/2001 | Zadno-Azizi et al. |
| 6,328,689 B1 | 12/2001 | Gonzalez |
| 6,355,014 B1 | 3/2002 | Zadno-Azizi et al. |
| 6,398,775 B1 | 6/2002 | Perkins et al. |
| 6,402,754 B1 | 6/2002 | Gonzalez |
| 6,416,554 B1 | 7/2002 | Alferness et al. |
| 6,428,561 B1 | 8/2002 | Johansson-Ruden et al. |
| 6,439,233 B1 | 8/2002 | Geertsema |
| 6,447,530 B1 * | 9/2002 | Ostrovsky et al. ............ 606/200 |
| 6,458,076 B1 | 10/2002 | Pruitt |
| 6,485,407 B2 | 11/2002 | Alferness et al. |
| 6,488,673 B1 | 12/2002 | Laufer et al. |
| 6,491,706 B1 | 12/2002 | Alferness et al. |
| 6,493,589 B1 | 12/2002 | Medhkour et al. |
| 6,503,272 B2 | 1/2003 | Duerig et al. |
| 6,510,846 B1 | 1/2003 | O'Rourke |
| 6,514,290 B1 | 2/2003 | Loomas |
| 6,527,761 B1 | 3/2003 | Soltesz et al. |
| 6,568,387 B2 | 5/2003 | Davenport et al. |
| 6,569,166 B2 | 5/2003 | Gonzalez |
| 6,585,639 B1 | 7/2003 | Kotmel et al. |
| 6,592,594 B2 | 7/2003 | Rimbaugh et al. |
| 6,599,311 B1 | 7/2003 | Biggs et al. |
| 6,610,043 B1 | 8/2003 | Ingenito |
| 6,629,951 B2 | 10/2003 | Laufer et al. |
| 6,634,363 B1 | 10/2003 | Danek et al. |
| 6,638,285 B2 | 10/2003 | Gabbay |
| 6,679,264 B1 | 1/2004 | Deem et al. |
| 6,682,520 B2 | 1/2004 | Ingenito |
| 6,694,979 B2 | 2/2004 | Deem et al. |
| 6,709,401 B2 | 3/2004 | Perkins et al. |
| 6,712,812 B2 | 3/2004 | Roschak et al. |
| 6,722,360 B2 | 4/2004 | Doshi |
| 6,743,259 B2 | 6/2004 | Ginn |
| 6,749,606 B2 | 6/2004 | Keast et al. |
| 6,929,637 B2 * | 8/2005 | Gonzalez et al. .......... 604/890.1 |
| 6,941,950 B2 | 9/2005 | Wilson et al. |
| 7,011,094 B2 * | 3/2006 | Rapacki et al. .......... 128/207.15 |
| 7,141,046 B2 | 11/2006 | Perkins et al. |
| 7,175,644 B2 | 2/2007 | Cooper et al. |
| 7,357,795 B2 | 4/2008 | Kaji et al. |
| 7,412,977 B2 | 8/2008 | Fields et al. |
| 7,476,203 B2 | 1/2009 | DeVore et al. |
| 7,887,585 B2 * | 2/2011 | Gonzalez et al. ................ 623/9 |
| 7,942,931 B2 | 5/2011 | Gonzalez et al. |
| 2002/0077593 A1 | 6/2002 | Perkins et al. |
| 2002/0077696 A1 | 6/2002 | Zadno-Azizi et al. |
| 2002/0095209 A1 | 7/2002 | Zadno-Azizi et al. |
| 2002/0112729 A1 | 8/2002 | Devore et al. |
| 2002/0147462 A1 | 10/2002 | Mair et al. |
| 2003/0018327 A1 | 1/2003 | Truckai et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0127090 A1 | 7/2003 | Gifford et al. |

| | | | |
|---|---|---|---|
| 2003/0154988 A1 | 8/2003 | Devore et al. | |
| 2004/0010209 A1 | 1/2004 | Sirokman | |
| 2005/0033344 A1* | 2/2005 | Dillard et al. | 606/191 |
| 2009/0188508 A1* | 7/2009 | Smith, Jr. | 128/207.14 |

FOREIGN PATENT DOCUMENTS

| | | |
|---|---|---|
| GB | 2324729 A | 11/1998 |
| RU | 2140211 | 10/1999 |
| SU | 852321 | 8/1981 |
| WO | WO 98/48706 | 11/1998 |
| WO | WO 00/51510 | 9/2000 |
| WO | WO 00/62699 | 10/2000 |
| WO | WO 00/78386 | 12/2000 |
| WO | WO 00/78407 | 12/2000 |
| WO | WO 01/02042 | 1/2001 |
| WO | WO 01/03642 | 1/2001 |
| WO | WO 01/05334 | 1/2001 |
| WO | WO 01/10313 | 2/2001 |
| WO | WO 01/10314 | 2/2001 |
| WO | WO 01/12104 | 2/2001 |
| WO | WO 01/13839 | 3/2001 |
| WO | WO 01/13908 | 3/2001 |
| WO | WO 01/28433 | 4/2001 |
| WO | WO 01/45590 | 6/2001 |
| WO | WO 01/49213 | 7/2001 |
| WO | WO 01/52775 | 7/2001 |
| WO | WO 01/54585 | 8/2001 |
| WO | WO 01/54625 | 8/2001 |
| WO | WO 01/54685 | 8/2001 |
| WO | WO 01/66190 | 9/2001 |
| WO | WO 01/74271 | 10/2001 |
| WO | WO 01/87170 | 11/2001 |
| WO | WO 01/89366 | 11/2001 |
| WO | WO 01/95786 | 12/2001 |
| WO | WO 02/05884 | 1/2002 |
| WO | WO 02/22072 | 3/2002 |
| WO | WO 02/32333 | 4/2002 |
| WO | WO 02/34322 | 5/2002 |
| WO | WO 02/38038 | 5/2002 |
| WO | WO 02/47575 | 6/2002 |
| WO | WO 02/056794 | 7/2002 |
| WO | WO 02/064045 | 8/2002 |
| WO | WO 02/064190 | 8/2002 |
| WO | WO 02/069823 | 9/2002 |
| WO | WO 02/094087 | 11/2002 |
| WO | WO 03/022124 | 3/2003 |
| WO | WO 03/030975 | 4/2003 |
| WO | WO 03/034927 | 5/2003 |
| WO | WO 03/041779 | 5/2003 |
| WO | WO 03/047468 | 6/2003 |
| WO | WO 03/078579 | 9/2003 |
| WO | WO 03/088820 | 10/2003 |
| WO | WO 03/099164 | 12/2003 |

OTHER PUBLICATIONS

Ellis, James H., Balloon Catheter Occlusion of Brochopleural Fistulae, May 7, 1981, AJR: 138, Jan. 1982, p. 157-159.

EWS Endobronchial Watanabe Spigots, Novatech, edited Apr. 17, 2002.

Horiuchi et al: Three Cases of Intractable Pneumothorax Treated Successfully by Bronchial Embolization using Silicon; JJSB, 2001. pp. 25-30.

Inaspettato: Endoscopic Treatment of Bronchopleural Fistulas Using N-butyl-2-cyanoacrylate; Surgical Laparoscopy & Endoscopy; vol. 4 No. 1, pp. 62-64, 1994.

International Search Report and Written Opinion for Application No. PCT/US2004/025458 mailed Nov. 30, 2004.

Jones et al: Closure of a Benign Broncho-Oesophageal Fistula by Endoscopic Injection of Bovine Collagen, Cyanocrylate Glue and Gelfoam; 1996, pp. 53-55 Aust. N.Z. J. Surg.

Lewis et al., "Pulmonary Interstitial Emphysema: Selective Bronchial Occlusion with a Swan-Ganz Catheter." Archives of Disease in Childhood, 63:1988, 313-315.

Mathew et al. "Selective Bronchial Obstruction for Treatment of Bullous Interstitial Emphysema," J. of Ped. 96:1980, 475-477.

Okada et al: Emergent Bronchofiberoptic Bronchial Occlusion for Intractable Pneumothorax with Severe Emphysema; The Japanese Journal of Thoracic and Cardiovascular Surgery, 1998. pp. 1078-1081.

Puhakka et al., "Acute Bronchial Obstruction: An Experimental Rabbit Model Study." Int. J. of Pediatric Otorhinolaryngology. 18:1989, 107-118.

Snider et al., "The Definition of Emphysema: Report of the National Heart Lung and Blood Institute, Division of Lung Diseases PCTrkshop", Am. Rev. Respir. Dis., 132:182-185, 1985.

Watanabe et al: Bronchial Embolization Using Dental Impression Material in a Case of Pyelo-bronchial Fistula with Candida Fungemia; 1991. Journal of the Japan Society for Bronchology, pp. 607-610.

* cited by examiner

BRONCHOSCOPIC REPAIR OF AIR LEAKS IN A LUNG

CLAIM OF PRIORITY

This application is a continuation application of U.S. patent application Ser. No. 12/398,122, filed Mar. 4, 2009, and incorporated in its entirety by reference herein, which is a divisional application of U.S. patent application Ser. No. 10/745,401, filed Dec. 22, 2003, and incorporated in its entirety by reference herein, and which claims the benefit of U.S. Provisional Application No. 60/493,933, filed Aug. 8, 2003, which is incorporated in its entirety by reference herein.

BACKGROUND

1. Field of the Invention

The invention relates in general to the field of pulmonary treatments, and specifically to a bronchoscopic method of treating air leaks in a lung.

2. Description of the Related Art

Air leaks that allow air inhaled through a person's mouth to leak out of a lung and into the pleural cavity or other cavity within the person's chest are frequently experienced by people with severe emphysema or other chronic pulmonary disorders. In the pathology of air leaks, there is a disruption of the lung pleura, parenchyma (tissue) and airways producing abnormal direct communication of inspired air to the thoracic cavity. Also, air leaks are a common complication of lung surgery and lung trauma. This undesired flow of air into the pleural cavity can ultimately lead to severe pneumothorax and collapse of the lungs caused by the loss of the normal pressure differential between the pleural cavity and the lung. Alveolar-pleural fistulas refer to a communication between the lung parenchyma and the pleural space and is commonly observed after trauma or in patients with weak and diseased lungs. Broncho-pleural fistulas are communications between the mainstream lobar, lobar or segmental bronchus and the pleural space and in many cases are consequence of surgery.

Typical treatment of air leaks involves the placement of chest tubes connected to a water trap/seal system to allow the leaked air to be drained from the pleural cavity in order to prevent tension pneumothorax and hopefully reverse the collapse of the lung. Some air leaks heal quickly within a few days without the need for intervention. Others, however, can take weeks or longer, while still others ultimately require surgery to resolve the leak.

Some bronchoscopic solutions have been developed for treatment of air leaks. For example the use of various plugs, glues, adhesives, and sealing agents have been used, with limited success. One problem with such occlusive devices is that they tend to dislodge from the patient's lung when the patient coughs. Thus, there remains a need for improvements to bronchoscopic air leak treatment procedures and systems.

SUMMARY OF THE INVENTION

The present invention addresses that need. Thus, one embodiment of an improved system for treating air leaks comprises means for identifying and sizing the lung airways that lead to the air leak, means for occluding those select airways to permit the leak to heal, and means for delivering and removing the occluding device as desired. An improved method comprises identifying and sizing lung airways that lead to the air leak, including identifying the fistula causing the air leak, delivering an occluding device to one or more of those airways to permit the air leak to heal, and removing the occluding device after the air leak has healed.

With regard to the present inventive system, the means for identifying the lung airways to be occluded is preferably, but not necessarily, a balloon catheter adapted to be used for identification and mapping of the airways communicating with a disrupted area of a lung. The balloon catheter may also be used as well to size the identified airways to select an appropriately sized intra-bronchial occlusion device for treatment. In the preferred embodiment, the occlusion device is a one-way valve expandable into place within the select airways, such as the devices disclosed in co-pending application Ser. Nos. 09/951,105; 10/317,667; 10/103,487; 10/124,790; 10/143,353 and 10/150,547, all of which are incorporated herein by reference. In an alternative embodiment, the occlusion device need not be a valve, but can be a device that precludes any fluid communication therethrough. In either case, it is preferred that the occlusion device include anchoring means, such as barbs, to preclude dislodging of the occlusion device once positioned in place. Valve action also minimizes dislodging by permitting the venting of some back pressure otherwise built up when the patient coughs.

If desired, medicants can be embedded in and/or coated on the occluding device. Alternatively or in addition, once the occluding device is in place, medicants could be injected into the airway on a distal side of the device to facilitate and/or accelerate the sealing and closure of the leaks.

The methods described herein involve minimally invasive procedures for treating air leaks in a patient's lung, including conditions created by alveolar-pleural fistulas and bronchopleural fistulas. There are many advantages to treating an air leak by deploying an occlusion device in a bronchial passageway. Providing a bronchial occlusion upstream from an air leak in accordance with the present methods can cause the air leakage out of the lung to be slowed, or preferably stopped. This will generally result in a reduction, elimination or prevention of pneumothorax caused by the air leak. At the same time, the reduction or elimination of airflow through the fistula is expected to allow the tissue surrounding the fistula to heal more quickly, thereby permanently closing the air leak.

As used herein, the term "air leak" is a broad term, and is used in its ordinary sense and refers, without limitation, to any flow of air exiting a lung by any unintended or undesired path. Also, as used herein, the term "fistula" is a broad term, and is used in its ordinary sense and refers, without limitation, to an abnormal passage providing fluid communication between a lung airway an another organ or cavity within a patient. For example, a fistula as referred to herein may generally include peripheral bronchopleural fistulas, bronchocutaneous fistulas, or any other fistulas causing an air leak. Such fistulas can be caused by trauma, thoracic surgery, irradiation, or disease such as necrotizing pneumonia, empyema, emphysema, etc. The methods and devices described herein are intended to be useful in treating air leaks, regardless of their specific cause.

As used herein, the terms "occlusion device" and "intra-bronchial occlusion device" are broad terms, and are used in their ordinary sense and refer, without limitation, to any object deployed in an airway that occludes the flow of air in either inspiratory or expiratory directions (or both) through the airway in which the device is deployed. The term is intended to include valves, plugs, ball bearings, injectable occluding substances such as glues or polymers, or any other object capable of occluding an airway.

DETAILED DESCRIPTION

Figure 1:
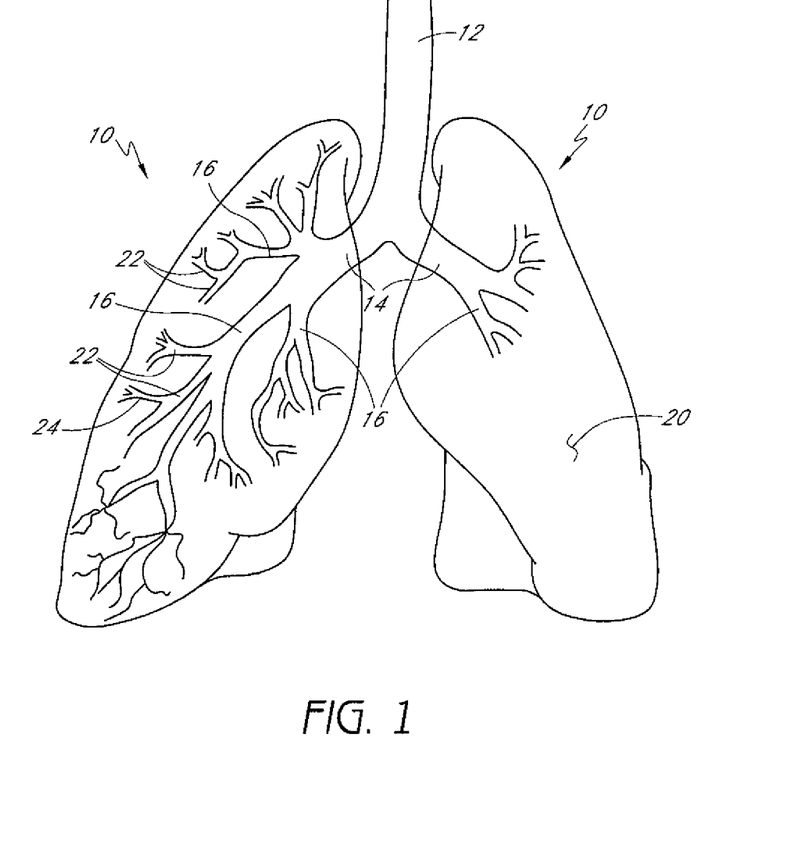
FIG. 1 is a schematic view of a pair of lungs.

Reference is now made to the figures wherein like parts are designated with like numerals throughout. Referring to FIG. 1, airflow in a lung 10 to be treated generally follows a path from the trachea 12, through the main branch bronchial tubes 14, then through the first generation sub-bronchial tubes 16 and ultimately to the numerous tiny bronchioles 18. The bronchioles 18 lead to alveolar sacs which function to transfer oxygen from the air to the bloodstream. The outer surface 20 of the lung comprises the parenchyma, sub-serous coat and serous coats that seal air within the lung. Air leaks as described herein can be caused by a breach of the parenchyma, the sub-serous coat and/or the serous coat that creates an abnormal passage between the interior air-passageways of the lung and the fluids and tissues external to the lung.

As used herein, the term "generation" is a broad term, and is used in its ordinary sense and refers, without limitation, to a location of an airway within a lung in terms of a number of bifurcations that are traversed in accessing a particular airway from the mainstem bronchus. For example, as shown in FIG. 9, the trachea 12 branches into the right and left mainstem bronchi 14. The mainstem bronchi 14 then branch into a plurality of first generation airways 16. Each of these first generation airways 16 then also branches into second generation airways 22 which in turn branch into third generation airways 24, and so on. As will be clear to the skilled artisan, the airways get progressively smaller in diameter as they progress to higher generations until the airways terminate in the alveoli.

Figure 2:
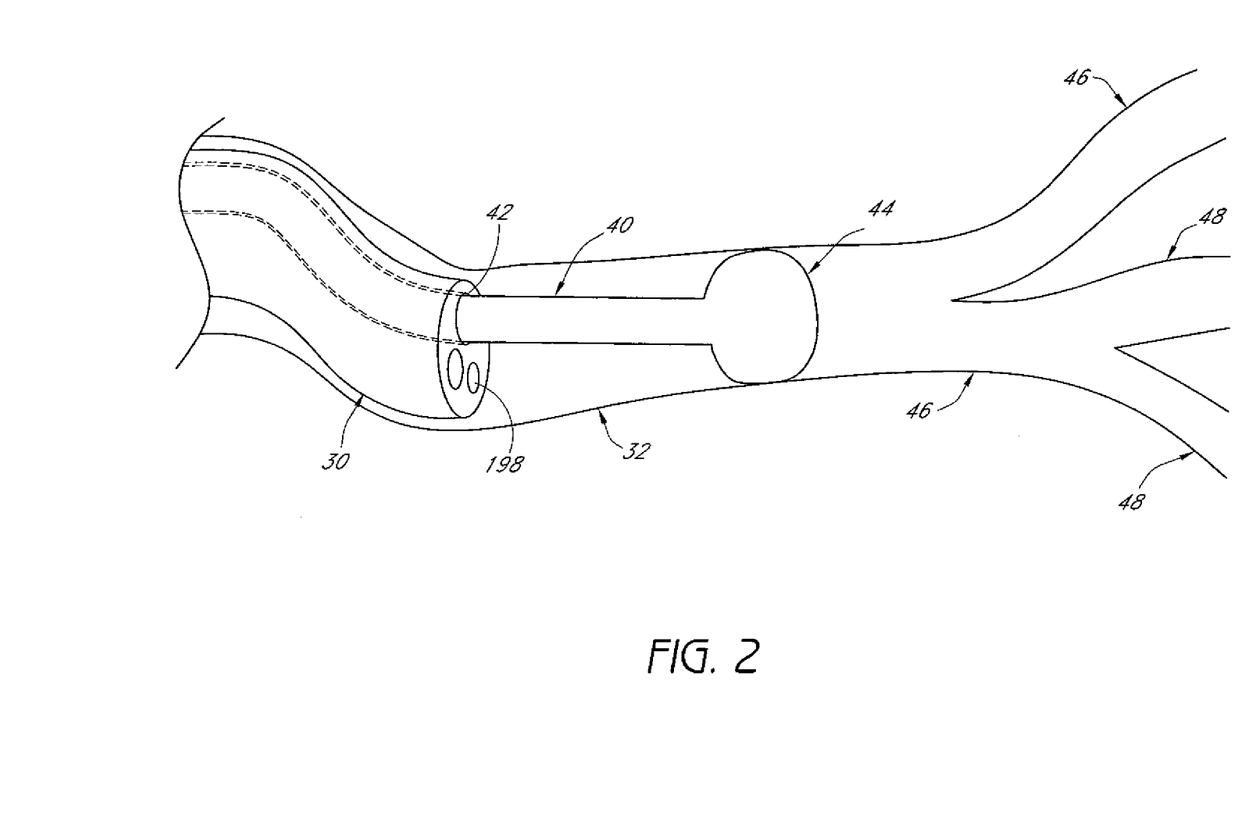
FIG. 2 is a cross-section of a lung portion schematically illustrating a delivery and deployment system.
Figure 3:
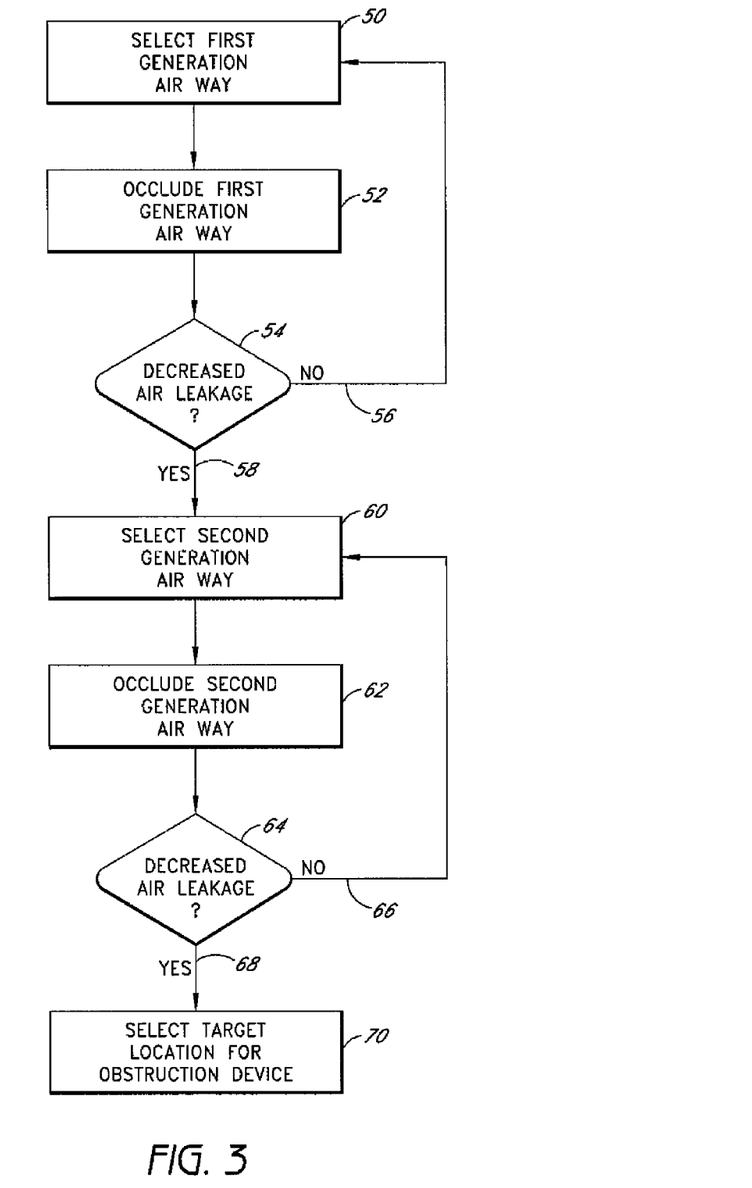
FIG. 3 is a flow chart illustrating one embodiment of a method of mapping and selecting airways in fluid communication with an air leak.

With reference to FIGS. 1-3, the preferred method comprises the steps of detecting the presence of an air leak in a lung, including identifying at least one airway leading to a fistula causing the air leak; selecting a target location; introducing a means for delivering an intra-bronchial occlusion device to the target location; optionally injecting a substance into the airway distal to the target location, and substantially limiting air leakage by temporarily deploying one or more occlusion devices for a sufficient time to allow the tissue surrounding the fistula to heal and close the fistula, and finally removing the occlusion device at some later time.

Methods for detecting the presence of air leaks in a human lung are generally well known, and any suitable method can be used in connection with the treatment systems and methods described herein. For example, the presence of an air leak in a lung can be identified by a physician on the basis of the patient's symptoms. In addition, some mechanical systems have been developed for the purpose of identifying air leaks in patients after thoracic surgery. For example, one such system is described in co-owned and co-pending patent application Ser. No. 10/259,007, filed on Sep. 26, 2002 which is incorporated herein by reference.

A means for identifying an airway in fluid communication with the fistula and for selecting a target location at which to deploy an intra-bronchial device can include any suitable device or system capable of doing so. In some embodiments, such systems involve testing airways in a trial-and-error manner by occluding a test airway and checking for a decrease in a flow rate and/or a volume of air leakage during each breath. The patient will often have a chest tube and a water trap or another suitable system in place to allow excess air in the patient's chest cavity to be drained. When the air-flow through the fistula is occluded, the lack of air-flow through the water trap (or other drainage system) can be observed, such as by a lack of, or a decrease in the number of bubbles in a water trap system.

According to one embodiment, an approximate location of a fistula is determined by x-ray or other imaging system, and then a bronchoscope is directed to a portion of the interior of the lung that is believed to be upstream of the fistula. A balloon catheter can then be directed through a working channel of the bronchoscope such that the inflatable balloon extends from the distal end of the bronchoscope. The balloon catheter is preferably configured such that inflation of the balloon is capable of completely occluding the airway in which it is positioned, thereby allowing a clinician to identify airways in fluid communication with the air leak and to determine whether the location of the balloon is a suitable location for an occlusion device. This determination is generally made by observing a cessation of, or a reduction in, the airflow through the chest tube and drainage system when the balloon is inflated to occlude the potential target airway. The reduction or cessation of air-flow through the drainage system (visible as a reduction in the number of bubbles in a water trap, for example) generally indicates that the undesired airflow through the fistula and into the pleural cavity has decreased or stopped. In some situations, it may be particularly beneficial to occlude a plurality of airways in order to reduce air leakage sufficiently to treat one or more fistulas. In general, it is desired that the occlusion device, or devices be placed as close to the periphery of the lung as possible. The closer to the actual fistula that an intra-bronchial device can be deployed, the smaller the amount of healthy lung tissue that will be occluded.

While attempting to select a suitable target location, the inflatable balloon 44 (see FIG. 2) used to temporarily occlude the airway can also be simultaneously used to measure a diameter of the airway at the potential target location and any other test locations identified during the process of selecting a target location. For example, when a relationship between a known volume of fluid used to inflate a balloon and a cross-sectional area of the balloon is known, the diameter of an airway at a proposed target location can be determined by measuring a volume of fluid required to inflate the balloon sufficiently to occlude the airway and to cause a reduction in the airflow through the drainage system. Further systems and methods for measuring a size of an airway with an inflatable balloon are described, for example, in co-owned and co-pending application Ser. Nos. 10/254,392 filed on Sep. 24, 2002 and 10/196,513 filed on Jul. 15, 2002, both of which are incorporated herein by reference and made part of the present application.

With reference now to FIGS. 1-3, embodiments of methods of locating and mapping airways in fluid communication with an air leak in a patient's lung will be described. According to one embodiment, a method of identifying and mapping airways in fluid communication with an air leak includes delivering a bronchoscope 30 into a first bronchial passageway 32 that is believed to be in communication with the leak. The first passageway 32 to be tested is typically a first or second generation airway. A balloon catheter 40 such as those described above can be fed through the working channel 42 of the bronchoscope 30 until the inflatable balloon 44 is in an airway 32. The balloon 44 is then inflated sufficiently to occlude airflow through the airway 32 to be tested. The balloon 44 is left in place while the patient inhales and exhales a few times.

FIG. 3 is a flow chart schematically illustrating one embodiment of a method for identifying and mapping airways in fluid communication with an air leak in a patient's lung. A clinician begins by selecting 50 a first test airway (a first generation airway in the illustrated example). The clinician then guides a bronchoscope 30 and/or a balloon catheter 40 to the selected test airway, and the clinician inflates the balloon 44 and occludes 52 the test airway. To determine whether or not the test airway is in fluid communication with the air leak, the clinician checks 54 for a decrease in a rate and/or a per breath volume of air leakage (using any suitable method or means). If the clinician does not detect 56 a decrease in air leakage, the clinician can repeat the selecting 50, occluding 52 and checking 54 steps until a first generation airway in fluid communication with the air leak is identified.

Once the checking step 54 returns a positive result 58 (i.e. a decrease in air leakage is detected), the clinician will advance the catheter to select a second 60, typically smaller, test airway (a second generation airway in the illustrated example). Once a second generation test airway is selected 60, it can be occluded 58 by inflating the balloon, and the clinician can check 64 for a further reduction in air leakage. Third, fourth and further generation airways in fluid communication with an air leak can be identified in much the same manner as described above with respect to the first and second. For example, when a second airway is occluded 62, a clinician can check for a decrease in air leakage 64. If the clinician finds no reduction in leakage 66, he/she can select 60 another second generation test airway and occlude it 62. Once a positive result 68 is returned, a clinician might determine that an optimum airway has been found, and he/she may select a target location 70 for deployment of an occlusion device.

In this way, a clinician can progressively narrow down the selection of airways in order to identify an optimum location for treating the air leak. Once a clinician has identified an optimum airway for treating the air leak, the clinician can select 70 that airway as a target location for the delivery of an intra-bronchial occlusion device as described herein.

In one embodiment, an optimum target location is preferably the smallest possible airway in fluid communication with the air leak, and in which an occlusion device can be deployed. In an alternative embodiment, an optimum target location is the airway which, when occluded, causes a maximum reduction in a rate of air leakage, while occluding a minimum of healthy lung tissue. In further embodiments, still other criteria can be applied for the selection of an optimum target location. In some embodiments, a clinician might determine a need for a plurality of occlusion devices, in which case, the clinician will typically identify a plurality of target locations.

As suggested above, the volume of fluid injected into the balloon 44 during the selection and mapping process can be correlated to a size of an occlusion device to be deployed at a selected target location. In this way, the occlusion device to be delivered can advantageously be selected to match the diameter of the target airway as closely as possible.

Additionally, throughout the selection process, the airways can also be mapped in terms of their size, generation, and their relative location. For example, each time an airway is occluded 52, 62, the volume of fluid injected into the balloon 44 can be recorded and correlated to an internal diameter of the airway at the test location. This size information can be useful for creating a graphic, schematic, or mathematic "map" of the airways in a patient's lung. Size information can also be combined with information relating to the generation of an airway, and where the airway is located relative to other known airways.

Thus, by measuring diameters of airways at a plurality of locations during the selection process, and/or by recording the location of each of the test locations, a map of the airways in fluid communication with an air leak in patient's lung can be developed. In mapping the airways in a patient's lungs, a clinician can gather information relating to the location of airways, such as by recording a length of the bronchoscope 30 and/or balloon catheter 40 advanced into the patient to reach a given test location, as well as a chosen direction each time a bifurcation is encountered. All of this location and size information can then be compiled in a three-dimensional map, a two-dimensional schematic map, or simply as a series of coordinates for the purpose of identifying the locations of each of the test points. Such a map can be useful in later navigating a catheter through a patient's airways to a target location (or any other recorded point) such as for removing an occlusion device, for later placing additional occlusion devices, or for other procedures requiring a clinician to navigate a bronchoscope through a patient's airways to a known point.

Once a target location has been selected 70, the location can be marked such that a clinician can later place an intra-bronchial occlusion device at substantially the same location that was measured with the inflatable balloon. Such marking can be performed by injecting a biocompatible visible ink or other visually-identifiable substance. Alternatively, the marking of a target location can be accomplished by providing markings on proximal ends of the balloon catheter and the delivery catheter. Alternatively still, a target location can be marked in such a way as to be visible via X-ray or other visualizing system. Alternatively, a target location can be recorded in a graphical or mathematical map which can be later followed by a clinician in order to guide a bronchoscope to deliver an occlusion device at a previously-selected target location.

The occlusion device is configured to substantially preclude inspired air or fluid downstream of said device, and in one embodiment comprises a one-way valve that allows the flow of fluid, whether gas or liquid, in one direction and substantially precludes fluid flow in an opposite direction. According to one embodiment, a one-way valve may be configured in the shape of an umbrella comprising an impermeable membrane surrounding a frame that is configured to exert radial forces against the wall of the airway passage. Such an arrangement would preclude substantial inspired air to the lung downstream of the placement of the device, but permit some limited fluid flow upstream, such as experienced with mucoscilliary transport or exhaled air. In another configuration, the one-way valve may comprise a stent-supported valve comprising an expandable support member mounted to a valve member. In still another configuration, the device may comprise an expandable frame with spherical or spheroid (egg) shape partially or completely covered with a membrane, such as the device described in co-pending application Ser. No. 09/951,105 identified above.

The occlusion device can be one of many devices suitable for occluding the flow of air in an anatomical lumen. For example, co-owned U.S. Pat. No. 6,293,951 to Alferness et al. shows and describes a number of devices for unidirectionally and bidirectionally occluding airflow through an airway. Additionally, co-owned and co-pending U.S. patent application Ser. No. 10/143,353 filed on May 9, 2002 shows and describes embodiments of a one-way valve that can also be used to treat an air leak while advantageously allowing mucous and other fluids to be moved proximally past the valve. Further embodiments of implantable one-way valves are described in co-owned and co-pending U.S. patent application Ser. Nos. 09/951,105 to Alferness et al. filed on Sep. 11, 2001; 10/103,487 to Alferness et al. filed on Mar. 20, 2002; 10/124,790 to DeVore filed on Apr. 16, 2002; and 10/150,547 to Dillard et al., filed on May 17, 2002. The entire disclosures of the above patents and applications are incorporated herein by reference and made part of the present disclosure.

In providing an occlusion device to be deployed in an airway for treating an air leak in a lung, it is believed to be substantially advantageous to provide a device configured to act as a one way valve by allowing air to flow past the device in an expiratory (or proximal) direction, while occluding airflow in an inspiratory (or distal) direction. For example, a one-way valve deployed in an airway for sealing an air leak has substantially less chance of being dislodged by the patient's coughing. In the case of a complete occlusion, a patient's cough will typically cause a substantial amount of air pressure to be built up at the distal edge of the occlusion relative to a pressure on proximal side. If this pressure differential is high enough, the occlusion device can become dislodged, and can actually be coughed out of the patient's mouth. In addition, the expansion and contraction of the lung tissue surrounding a deployed occlusion device can cause some occlusion devices to migrate within the airway, and potentially to become dislodged. By allowing expired air to flow out past the device, the pressure differential between the distal side and the proximal side of the device will typically not reach a level sufficient to dislodge the device. Nonetheless, by employing anchors, even a non-valvular occlusion device can be maintained in the desired target position.

Additionally, an occlusion device to be deployed in an airway for the treatment of an air leak is preferably configured to have a minimum effect on the lung's mucosciliary transport. For example, as mentioned above, the co-owned and co-pending application Ser. No. 10/143,353 teaches embodiments of occlusion devices which could be used in accordance with the methods described herein.

One preferred embodiment of an occlusion device, illustrated in FIGS. 4-8, comprises an intra-bronchial valve (IBV) 140 for use in treating an air leak. The illustrated valve 140 is preferably generally umbrella-shaped and comprises a frame 142 having a plurality of struts 144 and preferably a plurality of anchor members 150, all of which are joined together at a central joint 152. The struts 144 are generally configured to support a membrane 160 on their outer surface 162. The IBV 140 is also illustrated as including a central connector rod 170 adapted to be engaged in deploying and removing the IBV 140.

As illustrated, the frame 142 may comprise a shape similar to an assymetric hourglass, with one end provided with a membrane and configured to act as a valve member, and the other end configured to anchor the device against axial movement within an airway. According to one embodiment, the frame 142 (including the struts 144 and the anchors 150) can be made of a single tubular piece of a superelastic material such as Nickel-Titanium (also known as NiTi or NITINOL). The frame 142 can be machined, molded, or otherwise formed to create the desired functional elements as shown and described herein. In one embodiment, a hollow tube of NiTi is machined to form the struts 144 and anchors 150. The struts and anchors can be formed from the solid tube by making axial cuts along the tube to create the desired number of struts 144 and anchors 150 while leaving an uncut ring section 172 between the struts 144 and the anchors 150. The struts 144 and anchors 150 can then be bent into the desired shapes in such a way that the frame will naturally assume the desired expanded shape at temperatures expected in an airway. Alternatively, the frame 142 can be made from sections of wire bent into the desired shapes. The skilled artisan will recognize that superelastic and/or "shape memory" materials such as NiTi typically require unique manufacturing processes involving substantial amounts of heat treating. The details of such manufacturing processes will be understood by those skilled in the art of Nickel-Titanium manufacturing.

Figure 4:
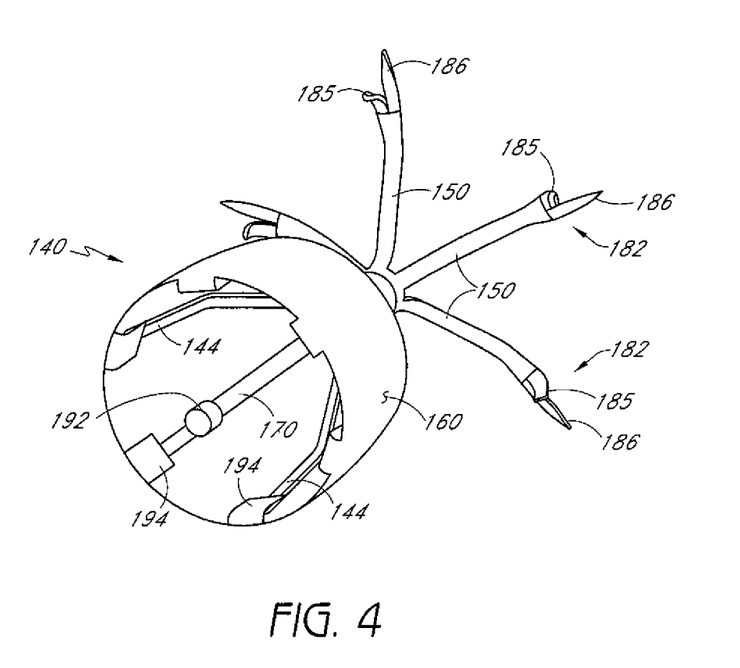
FIG. 4 is a perspective view of one embodiment of an intra bronchial occlusion device.
Figure 5:
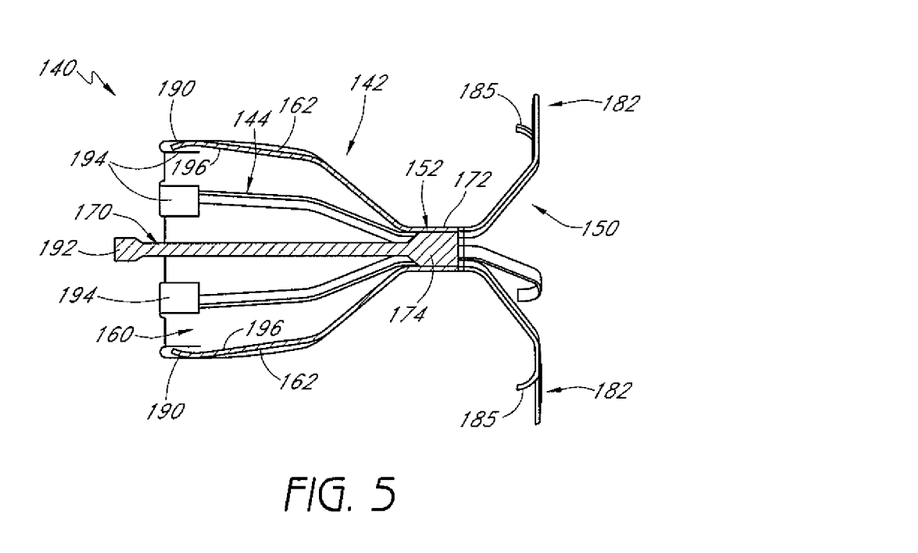
FIG. 5 is a cross-sectional view of the occlusion device of FIG. 4.

The connector rod 170 typically includes a base 174 that is sized to be attached to the ring section 172 of the frame 142 at the central joint 152. The attachment of the connector rod 170 to the frame 142 can be accomplished by press fitting the base 174 within the ring section 172 of the frame 142. If desired the connection between the rod base 174 and the ring section 172 can further include adhesives, welds, or any other suitable fastening means.

The frame 142 made of a superelastic material such as NiTi advantageously allows the IBV to be compressed to occupy a very small axial shape during delivery, and to be released to assume a substantially larger shape when deployed. Additionally, a frame made of a shape-memory material will remain substantially elastic in its expanded and installed shape. Thus, the IBV can be configured to have sufficient elasticity in its expanded shape to allow the IBV to expand and contract with the expansion and contraction of the bronchial walls 180, thereby maintaining the occlusion to distal airflow throughout repeated respiration cycles. Additionally, other intra-bronchial occlusion devices can be configured to expand and contract with the tissue of the bronchial walls.

In the illustrated embodiments, the frame 142 comprises six struts 144 and five anchors 150. Other numbers of struts and/or anchors can alternatively be used. For example, the number of struts 144 and anchors 150 may be equal, and each individual strut may comprise a unitary structure with an individual anchor member.

The distal ends of the anchor members 150 preferably comprise piercing tips 182 generally configured to puncture tissue of an air passageway wall 180 to retain the IBV 140 in a desired location within the airway. As shown in FIGS. 4-8, the piercing tips 182 can include stops 184 configured to prevent the anchor members 150 from puncturing through the lung tissue 180 beyond a desired depth. The stops 184 can be formed by splitting the distal ends of the anchor members 150, and bending a first one of the split sections downward to form the stop 184 as shown, while leaving a second one 186 of the split sections to extend outwards in order to puncture a section of tissue.

During inspiration, a substantial air pressure differential can be built up with a high pressure side on a proximal side of the valve. In the absence of any anchors, this pressure could potentially force the IBV distally within the airway. Therefore, it is desirable to anchor the IBV against at least distal movement within the airway. In general, the fact that the IBV will allow expiratory airflow in a proximal direction past the device means that there will be a substantially smaller pressure differential across the valve during expiration (including coughing). Thus, the anchor arrangement including piercing tips 182 and stops 184 of FIGS. 4-8 are advantageously arranged to primarily prevent distal movement of the IBV within the airway. The IBV will also be anchored against proximal movement by the resilience of the anchor members 150 and the strut members 144 pressing against the bronchial wall 180. Also advantageously, when the connector rod 170 of the IBV 142 is gripped and pulled proximally to remove the IBV from an airway, the anchors 150 will collapse slightly, and the piercing tips 182 will release from engagement with the bronchial wall 180 as the IBV is pulled proximally.

Figure 6:
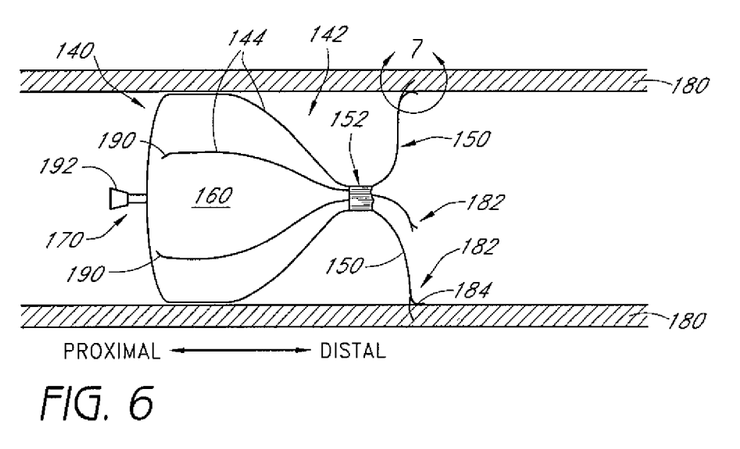
FIG. 6 is a side section view of an airway with an occlusion device deployed therein.
Figure 7:
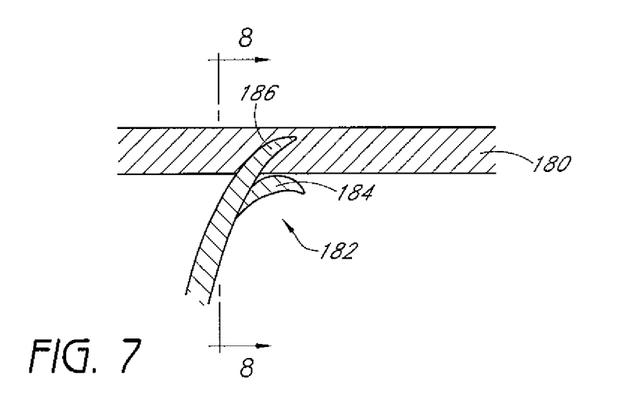
FIG. 7 is a detail view of a portion of the occlusion device of FIG. 6.
Figure 8:
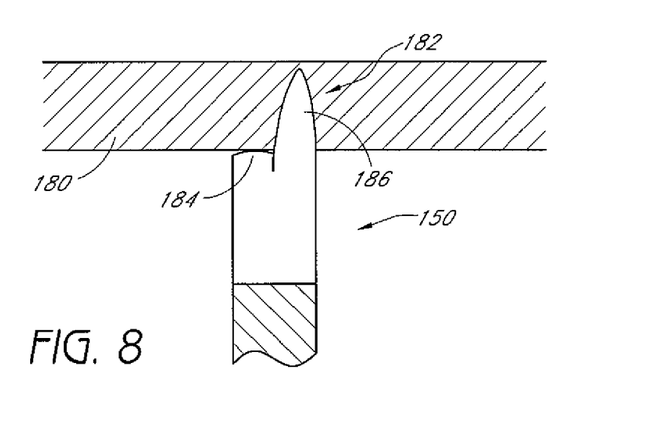
FIG. 8 is a front view in partial cross-section of the portion of FIG. 7.

As shown in FIGS. 5 and 6, the proximal ends 190 of the struts 144 curve slightly inwards. This inward curve will further aid in allowing easy removal of the IBV 140 from an airway by pulling the valve proximally. The inward curve of the proximal strut ends 190 will preferably substantially prevent the struts 144 from snagging the tissue of the airway walls as the IBV is drawn proximally.

The curved proximal strut ends 190 will also aid in guiding the IBV 140 into a constricting funnel-shaped lumen so as to compress the IBV for loading into a delivery catheter as is described, for example in the Ser. No. 10/387,963 application mentioned above. As discussed in the '963 application, one embodiment of loading the IBV into a deliver catheter comprises advancing the IBV, rod-end first into a funnel-shaped constriction. The inwardly curved proximal strut ends 190 will advantageously allow the IBV to be smoothly advanced through such a funnel-shaped constriction without damaging the IBV.

As illustrated in FIG. 5, the connector rod 170 extends from the central joint 152 proximally through the axial center of the IBV 140. In one embodiment, the rod 170 is of such a length that it extends beyond the proximal ends 190 of the struts 144 when the IBV 140 is in its expanded shape. The rod 170 can also be of such a length that the rod 170 and the struts 144 extend substantially the same distance from the central joint 152 when the IBV 140 is in a fully compressed state (not shown). The connector rod 170 can be made of a biocompatible stainless steel, PVC, or any other suitably rigid biocompatible material as desired. The connector rod 170 is preferably sufficiently rigid that when the proximal knob 192 of the rod 170 is gripped, the IBV can be rigidly supported in a cantilevered manner. The connector rod 170 is also preferably configured to facilitate removal of the IBV from an airway by gripping the proximal knob 192 of the rod 170 with standard or specially-designed forceps and pulling proximally on the rod 170.

The membrane 160 is generally made of a biocompatible polyurethane or other thin, air impermeable material. As shown in FIGS. 2 and 3, the membrane 160 can include tabs 194 which can be folded over the interior sides 196 of the proximal ends 190 of the struts 144. Covering the proximal ends 190 of the struts 144 with tabs 194 of membrane material advantageously prevents the struts 144 from digging into or snagging on the tissue of the bronchial wall, thereby aiding in removal of the IBV from an airway.

The membrane 160 can be formed from a single, flat sheet of air impermeable material which can be sealed to the frame by adhesives, welds, heat seals or any other suitable manner to create an air-tight seal between a first (proximal) side and a second (distal) side of the membrane. Alternatively, the membrane 160 could be molded or thermoformed into a desired shape which can then be sealed to the frame.

According to an alternative embodiment, the membrane 160 can be formed by placing a mandrel inside the concave space between the struts 144, and then dipping the entire frame 140 into a molten solution of a desired polymer. The frame can then be removed from the molten solution, and the polymer can be allowed to cool, thereby forming a uniform membrane that substantially entirely encases the struts. In some embodiments, the dipping process can also be employed to form a coating over each of the distal anchors, thereby substantially preventing contact between the metallic frame 140 and the patient's airway tissue. This can be advantageous in cases where a patient's tissues reject nickel-titanium or other material from which the frame is made.

Suitable occlusion devices can be provided in any size or configuration as desired. For example, in some embodiments, one-way valve occlusion devices having expanded outer diameters of between about 3 mm and about 8 mm can be used. Alternatively, valves having outer expanded diameters as small as 1 mm or less could be used.

With returned reference to FIG. 2, a means for delivering an intra-bronchial valve to a target location in an airway of a lung can include one of a number of known or newly developed devices. In one embodiment, means for delivery of an occlusion device to a target location comprises a conventional bronchoscope 30 having a visualizing tip 198 and at least one working lumen 42. A wide variety of bronchoscopes are commercially available, many of which will be suitable for carrying out portions of the air leak repair procedure described herein. Typical bronchoscopes have an outer diameter of about 5 mm, although larger or smaller bronchoscopes could also be used.

Alternatively, any number of other devices could be used in place of a conventional bronchoscope. Specifically, any device that allows a clinician to gain visual and functional access to the interior of a patient's lungs could be used. Such alternative devices could include laparoscopes, endoscopes, or any other elongate, flexible scope with at least one working lumen and/or one or more tools mounted on a distal end thereof. In addition to the visualizing capabilities of any bronchoscope (or other scope) that may be used, a clinician may decide to use X-ray, ultrasonic, radiographic, or other visualization systems to provide supplemental visualization during the air-leak treatment procedure.

Suitable means for delivering an intra-bronchial device to a target location often further includes one or more elongate, flexible catheters with one or more lumens extending therethrough. Suitable catheters preferably have as small an outside diameter as possible, while maintaining sufficient column strength for the catheter to be advanced through a patient's airways without buckling or kinking. For example, in some embodiments catheters may be provided with an outer diameter of about 2 mm, although larger and smaller catheters can also be used. At least one lumen of at least one catheter can be adapted to allow airflow therethrough. Similarly, at least one lumen of at least one catheter can be adapted to transmit a liquid therethrough.

Occlusion devices can generally be deployed using any suitably configured catheter. For example, an occlusion device deployment catheter can include a distal cavity for retaining at least one occlusion device to be deployed in a patient's airway and a means for deploying the occlusion device. A means for deploying the occlusion device can include any suitable structure such as a push wire that is extendable through the length of the catheter and can be operated by a clinician to push the occlusion device out of the catheter. Alternatively, the means for deploying the occlusion device could include a retractable sheath that can be retracted relative to the occlusion device, thereby releasing the occlusion device. In another alternative embodiment, one or more occlusion devices can be deployed directly from a lumen of a bronchoscope without the need for a delivery catheter. Suitable delivery and deployment devices are described in co-owned and co-pending U.S. patent application Ser. Nos. 10/052,875 filed Oct. 25, 2001 and 10/387,963 filed Mar. 12, 2003, both of which are incorporated by reference and made part of the present application.

Occlusion devices for use with embodiments of the methods described herein can generally be adapted to be removed from a patient's airway after the fistula or other air leak has healed. A means for removing an occlusion device can include an elongate, flexible removal catheter with an occlusion device receiving space, and a means for gripping the occlusion device. The occlusion device receiving space can simply be a lumen of sufficient diameter to allow an occlusion device to be drawn into the space. If desired, the occlusion device receiving space can be sized to receive a plurality of occlusion devices, thereby eliminating the need to remove and re-introduce the removal catheter when removing multiple occlusion devices. A means for gripping an occlusion device can include any suitable trans-lumenal gripping tool, such as biopsy forceps, etc.

Alternatively, a means for removing an occlusion device could simply include a bronchoscope. Accordingly, the occlusion device could be drawn into a lumen of the scope, for example by gripping the connector rod with standard endoscopic forceps, thereby allowing the occlusion device and the bronchoscope to be simultaneously removed. In alternative embodiments, portions of the occlusion devices can be made from a substantially bioabsorbable polymer which can be substantially dissolved and absorbed by a patient's body fluids and tissue, thereby allowing bi-directional airflow to be resumed through a target location without the need for bronchoscopic removal of an occlusion device.

The methods of the present invention can be carried out with the above devices or any other tools or devices recognized as suitable by the skilled artisan. One embodiment of the method generally includes: detecting the presence of an air leak in a lung; identifying an airway leading to a fistula causing the air leak; identifying and marking a target location within an airway; guiding a means for delivering an intra-bronchial device to the airway in fluid communication with a fistula causing the air leak, optionally injecting a substance into the airway distal to the target location, and substantially limiting air leakage by temporarily deploying one or more occlusion devices in selected airways for a sufficient time to allow the tissue surrounding the fistula to heal and close the air leak, and finally removing the occlusion device at some later time.

Methods of delivering an occlusion device are described in the Ser. Nos. 10/052,875 and 10/387,963 applications mentioned above. According to one embodiment, the occlusion device is loaded into a cavity at a distal end of an elongate delivery catheter. The delivery catheter of this embodiment is provided with a retractable sheath to surround and retain the occlusion device. The catheter can then be fed through the working channel of the bronchoscope, or otherwise directed to the previously-identified target location. Once the occlusion device is in place, the sheath surrounding the occlusion device can be retracted to allow the occlusion device to expand to its unrestrained shape and size.

As mentioned above, it may be desirable to inject a substance into an airway on the distal side of the deployed occlusion device. For example, such substances could include one or more medicants injected directly into an airway or associated with an intra-bronchial device in any appropriate manner. Co-owned and co-pending U.S. patent application Ser. Nos. 10/178,073 and 10/317,667, filed on Jun. 21, 2002 and Dec. 11, 2002 respectively, teach embodiments of methods and devices for delivering various medicants and therapeutic substances to a target location of a lung in order to accelerate healing, or otherwise control a biological interaction.

Alternatively, as described in co-owned and co-pending U.S. patent application Ser. No. 10/409,785 ("the '785 Application") filed on Apr. 8, 2003, which is also incorporated herein by reference, it is contemplated that injection of an inflammation-causing substance can aid in causing lung tissue to sclerose and self adhere. Such an inflammation-causing substance could also be used in treating an air leak by promoting sclerosis and healing of the lung tissue in the vicinity of the injected substance. According to one embodiment as described in the '785 application, the inflammation-causing substance injected into a lung portion can comprise or consist of autologous blood or a constituent thereof.

Alternatively still, other organic and non-organic substances, gaseous or liquid, heated or cooled, may be used to cause inflammation of the lung tissue adjacent to a fistula. For example, U.S. Patent Application Publication No. 2001/0051799 to Ingenito (incorporated in its entirety herein by reference, shows and describes a number of fibrosis-causing substances. Hot saline solution or very cold liquids or gasses may also be used.

In some situations it might be necessary to occlude an airway that feeds a substantial portion of healthy lung tissue in addition to the damaged section. It is preferred that the placement of the occlusion devices will occlude a minimum of airways extending through healthy lung tissue.

Once the occlusion device deployment and any substance-injection procedures have been completed, the bronchoscope and any other trans-bronchial tools can be withdrawn from the patient, thus leaving the occlusion device(s) and any injected substance in place relative to the fistula. The procedures described herein allow the patient to be ambulatory while the fistula heals. Depending upon the patient, the amount of damage and the particular substance injected (if any), the time required for the fistula to heal will vary. The occlusion device(s) can be removed after a clinician has verified that the fistula has substantially healed. Verification of air leak healing can be accomplished by evaluation of a patient's symptoms, testing a patient's breathing function (e.g. breathing effort, etc), and/or by imaging of a patient's lungs such as by x-ray or MRI scans.

Once the air leak has healed, a suitable means for removing an occlusion device can be introduced through the patient's airways to a position adjacent an occlusion device. Once in position, the means for removing an occlusion device can be operated in an appropriate manner to remove one or all of the occlusion devices. Multiple occlusion devices can be removed in any suitable sequence, and if desired, without removing a bronchoscope with each occlusion device. In an alternative embodiment, a frame and/or a membrane of an occlusion device can comprise a bio-absorbable polymer, which can be left in place and allowed to deteriorate, thereby "removing" the occlusion device from the path of air flow in the target section without introducing a bronchoscope or a removal catheter.

Although certain embodiments and examples have been described herein, it will be understood by those skilled in the art that many aspects of the methods and devices shown and described in the present disclosure may be differently combined and/or modified to form still further embodiments. Additionally, it will be recognized that the methods described herein may be practiced using any device suitable for performing the recited steps. For example, the target location air leak could be treated by the present method in combination with conventional open-chest or thoracoscopic surgical procedures. Such alternative embodiments and/or uses of the methods and devices described above and obvious modifications and equivalents thereof are intended to be within the scope of the present disclosure. Thus, it is intended that the scope of the present invention should not be limited by the particular embodiments described above, but should be determined only by a fair reading of the claims that follow.

What is claimed is:

1. A system for use in treating an air leak in a lung, the system comprising:
    a balloon catheter configured to occlude an airway and to simultaneously measure a diameter of the airway;
    a delivery catheter configured to deliver an obstruction device into an airway of the lung;
    at least one occlusion device adapted to occlude airflow in an inspiratory direction while allowing fluid to flow in an expiratory direction, wherein the occlusion device comprises a central connector rod extending proximally from a central portion thereof the occlusion device surrounding at least a portion of the central connector rod;
    the occlusion device being configured such that fluid flow in the expiratory direction passes between an airway wall and a portion of the occlusion device; and
    the occlusion device further being configured to expand and contract during expansion and contraction of surrounding lung tissue during a respiration cycle.

2. The system of claim 1, wherein the occlusion device comprises an hourglass-shaped frame.

3. The system of claim 2, wherein the hourglass-shaped frame comprises the central portion, a plurality of anchors extending radially outward and distally from the central portion, and a plurality of strut members extending radially outward and proximally from the central portion.

4. The system of claim 3, wherein the frame further comprises a flexible membrane supported by the strut members.

5. The system of claim 1, wherein the balloon catheter is sized to permit selection of one of a plurality of available obstruction members.

6. The system of claim 1, wherein the occlusion device comprises anchors extending radially outward and distally from the central portion.

7. The system of claim 6, wherein the anchors further comprise stops preventing the anchors from penetrating beyond a desired depth.

8. The system of claim 1, wherein the central connector rod comprises a knob disposed at a proximal end thereof.

* * * * *